United States Patent [19]

Ife

[11] Patent Number: 4,692,456
[45] Date of Patent: Sep. 8, 1987

[54] 3-PYRIDYLAMINOALKYLENEAMINO-4-AMINO-1,2,5-THIADIAZOLE-1-OXIDES, COMPOSITION CONTAINING THEM, AND USE OF THEM TO BLOCK HISTAMINE H₂-RECEPTORS

[75] Inventor: Robert J. Ife, Stevenage, England

[73] Assignee: Smith Kline & French Laboratories Limited, Welwyn Garden City, England

[21] Appl. No.: 838,972

[22] Filed: Mar. 12, 1986

[30] Foreign Application Priority Data

Apr. 11, 1985 [GB] United Kingdom ................. 8509276

[51] Int. Cl.⁴ ..................... A61K 31/44; A61K 31/41; C07D 417/12; C07D 417/14
[52] U.S. Cl. .................................. 514/333; 514/342; 546/256; 546/277
[58] Field of Search ................. 546/256, 277; 514/333, 514/342

[56] References Cited

U.S. PATENT DOCUMENTS

| | | | |
|---|---|---|---|
| 4,374,248 | 2/1983 | Crenshaw et al. | 548/135 |
| 4,394,508 | 7/1983 | Crenshaw et al. | 546/209 |
| 4,532,246 | 7/1985 | Ife | 514/275 |

*Primary Examiner*—Henry R. Jiles
*Assistant Examiner*—Kurt G. Briscoe
*Attorney, Agent, or Firm*—Linda E. Hall; Stuart R. Suter; Alan D. Lourie

[57] ABSTRACT

New 3,4-diamino-1,2,5-thiadiazole oxide derivatives which are histamine H₁-antagonists. A specific compound of this invention is 3-[3-(N-propyl-N-2-pyridylamino)-propylamino]-4-(4-pyridylmethyl)amino-1,2,5-thiadiazole-1-oxide.

18 Claims, No Drawings

3-PYRIDYLAMINOALKYLENEAMINO-4-AMINO-1,2,5-THIADIAZOLE-1-OXIDES, COMPOSITION CONTAINING THEM, AND USE OF THEM TO BLOCK HISTAMINE H₂-RECEPTORS

This invention relates to certain pyridine derivatives, pharmaceutical compositions containing them and a method of blocking histamine $H_1$-receptors by administering them.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine.

According to the present invention there is provided compounds of formula (1):

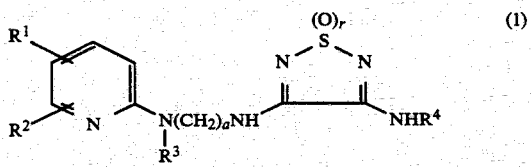

and pharmaceutically acceptable salts thereof, where
$R^1$ and $R^2$ are the same or different and are hydrogen, $C_{1-6}$alkyl, $C_{1-6}$alkoxy or halogen;
$R^3$ is $C_{1-6}$alkyl or optionally substituted phenyl or optionally substituted pyridyl, where the optionally substitutents are one or more $C_{1-6}$alkyl, $C_{1-6}$alkoxy, or hydroxy groups or halogen atoms;
a is from 2 to 4
$R^4$ is $(CH_2)_b R^5$ where b is 1–6 and
$R^5$ is
  phenyl optionally substituted by one or more $C_{1-6}$alkyl, $C_{1-6}$alkoxy, hydroxy, carboxy (or an ester thereof) or sulphonamido groups or halogen atoms;
  pyridyl optionally substituted by one or more $C_{1-6}$alkyl, $C_{1-6}$alkoxy or hydroxy groups or halogen atoms; or
  N-oxo-pyridyl optionally substituted by $C_{1-6}$alkyl; and
r is 1 or 2.

The compounds of this invention are histamine $H_1$-antagonists and are useful for the treatment of diseases for example bronchial asthma, rhinitis, hayfever and allergic eczema whose symptoms are mediated through the action of histamine at $H_1$-receptors.

Examples of halogens for $R^1$, $R^2$ and the halogen substituent in $R^3$ and $R^5$ are fluorine, chlorine, bromine and iodine.

Examples of $C_{1-6}$alkyl groups for $R^1$, $R^2$, and $R^3$ and the $C_{1-6}$alkyl substituent in $R^3$ and $R^5$ are methyl, ethyl, n-propyl, iso-propyl, n-butyl and t-butyl.

Examples of $C_{1-6}$alkoxy groups for $R^1$, $R^2$ and the $C_{1-6}$alkoxy substituents in $R^3$ and $R^5$ are methoxy, ethoxy, n-propoxy and n-butoxy.

Preferably $R^1$ and $R^2$ are both hydrogen.

By way of example, a can be 2, 3 or 4. Preferably it is 3.

Examples of substituted phenyl groups for $R^3$ and $R^5$ are the monosubstituted groups 2-methylphenyl, 2-methoxyphenyl, 2-chlorophenyl, 2-fluorophenyl, 3-methylphenyl, 3-methoxyphenyl, 3-chlorophenyl, 3-fluorophenyl, 4-methylphenyl, 4-methoxyphenyl, 4-chlorophenyl and 4-fluorophenyl.

Examples of optionally substituted pyridyl groups for $R^3$ and $R^5$ are optionally substituted 2-pyridyl, 3-pyridyl or 4-pyridyl groups, particularly monosubstituted groups.

In particular, $R^3$ is phenyl or $C_{1-6}$alkyl, preferably n-propyl.

Preferably b is 1.

Where $R^5$ is phenyl, examples of suitable ester substituents are $C_{1-6}$alkyl esters, particularly methyl and ethyl.

Where $R^5$ is phenyl, examples of suitable salts of the carboxyl group include in particular alkali metal salts, especially the sodium and potassium salts.

Where $R^5$ is phenyl substituted with a carboxyl group, the compound can exist in a zwitterionic form.

Preferably any carboxyl group or sulphonamido group in $R^5$ is in a position para to the point of attachment of the group —$(CH_2)_b$—.

Where $R^5$ is N-oxo-pyridyl, the group —$(CH_2)_b$— is attached in particular at position 4 of the pyridyl group.

Examples of particular values for $R^5$ when it is N-oxo-pyridyl are: 2-methyl-N-oxo-4-pyridyl and N-oxo-4-pyridyl.

Preferably $R^5$ is 4-carboxyphenyl, phenyl or 4-pyridyl.

Preferably r is 1.

Compounds of formula (1) also form pharmaceutically acceptable salts with pharmaceutically acceptable acid addition salt-forming acids. Accordingly, in this specification the term "pharmaceutically acceptable salts" means salts with bases or acid addition salts as the context requires.

Examples of pharmaceutically acceptable acid addition salt-forming acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

Compounds of formula (1) can be prepared by reacting an amine of formula (2):

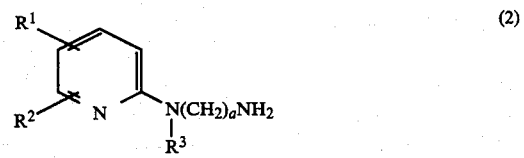

where $R^1$, $R^2$, $R^3$ and a are as defined with reference to formula (1) with a compound of formula (3):

where X is a group displaceable with an amine and $X^1$ is a group displaceable with an amine or a group of formula $NHR^4$ where $R^4$ is as previously defined, and where $X_1$ is a group displaceable with an amine, thereafter reacting with an amine of formula (4):

where $R^4$ is as defined with reference to formula (1).

Examples of leaving groups displaceable by amines are where X and $X^1$ are QS—, QSO—, QSO$_2$—, or QO— (Q being $C_{1-6}$alkyl, aryl or aralkyl), halogen, particularly chlorine and bromine, and nitroamino. Preferably the groups X and $X^1$ are QO— where Q is methyl.

The conditions under which the reaction is carried out depends upon the nature of the reagents. The reaction is carried out at moderate to low temperature e.g. from 0° C. to room temperature. The choice of solvent is affected by the solubility characteristics of the reagents. Preferably the solvent is pyridine, a picoline or mixture of picolines, a $C_{1-6}$alkanol, preferably methanol or 1-propanol, 1,2- ethanediol, a high boiling alkoxyaryl ether for example anisole, or a polar aprotic solvent, for example dimethylformamide, dimethylacetamide, dimethylsulphoxide, hexamethylphosphoramide or sulpholane.

Where $R^5$ in the compound of formula (1) is phenyl substituted with a carboxyl group, the carboxyl group can be converted into a pharmaceutically acceptable salt by standard methods for example by reacting the compound in solution with a solution of a base.

Where $R^5$ in the compound of formula (1) is a carboxyl group it can be converted into an ester by standard techniques for example esterification with an alcohol or an esterifying derivative of the alcohol.

Where $R^5$ in the compound of formula (1) is phenyl substituted with a carboxyl ester, the ester can be converted into a carboxyl group by standard techniques for example by a hydrolysis under basic conditions.

Pharmaceutically acceptable acid addition salts of compounds of formula (1) can be prepared by standard methods, for example by reacting a solution of the compound of formula (1) with a solution of the acid.

Compounds of formula (2) where $R^3$ is $C_{1-6}$alkyl can be prepared by reacting a compound of formula (5):

$$\underset{R^2}{\overset{R^1}{\diagdown}}\text{(ring)}\text{N}-\text{NH(CH}_2)_a\text{NH}_2 \quad (5)$$

where $R^1$ and $R^2$ and a are as defined with reference to formula (1) or a derivative thereof where the primary amino group is protected, with a compound of formula (6):

$$R^3X^2 \quad (6)$$

where $R^3$ is $C_{1-6}$alkyl and $X^2$ is halogen, in the presence of a strong base and thereafter removing any protecting groups.

Compounds of formula (5) can be prepared in turn by reacting a compound of formula (7):

$$\underset{R^2}{\overset{R^1}{\diagdown}}\text{(ring)}\text{N}-X^2 \quad (7)$$

where $R^1$ and $R^2$ are as defined with reference to formula (1) and $X^2$ is halogen with an amine of formula (8):

$$\text{NH}_2(\text{CH}_2)_a\text{NH}_2 \quad (8)$$

where a is as defined with reference to formula (1).

Compounds of formula (2) can also be prepared by reacting a compound of formula (9):

$$\underset{R^2}{\overset{R^1}{\diagdown}}\text{(ring)}\text{N}-\underset{R^3}{\overset{|}{\text{NH}}} \quad (9)$$

where $R^1$, $R^2$ and $R^3$ are as defined with reference to formula (1) (provided that any hydroxy groups in $R^3$ are protected) with a compound of formula (10):

$$X^2(\text{CH}_2)_a R^6 \quad (10)$$

where a is as defined with reference to formula (1), $X^2$ is halogen and $R^6$ is a protected amino group, in the presence of a strong base and thereafter removing any protecting groups.

Examples of hydroxy protecting groups are $C_{1-6}$ alkyl, for example methyl, and $C_{1-6}$alkanoyl, for example formyl or acetyl.

These protecting groups can be removed by standard methods, in particular under basic conditions.

Examples of protected amino groups for $R^6$ include phthalimido. In formulae (6), (7) and (10) $X^2$ can be chlorine, bromine or iodine.

Examples of strong bases are alkali metal hydrides, particularly sodium hydride. The reaction is carried out in the presence of a polar solvent for example dimethylsulphoxide.

The protected amino group can be converted into amino by standard methods, for example when it is phthalimido by reaction with hydrazine.

The use of protecting groups is discussed in J. F. McOmie, Protective Groups in Organic Chemistry, 1973, Plenum Press, IBSN 0-306-30717-0.

Compounds of formula (3) are known or can be made by known methods as described in for example British Patent Application No. 2067987A.

Compounds of formulae (4) and (6) to (10) are known or can be made by known methods.

The histamine H$_1$-antagonist activity of the compounds of formula (1) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of the Examples have $pA_2$ values greater than 7.

The activity of compounds of formula (1) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier or parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included. As in common practice, the compositions will usually be accompanied by written or printed directions for use in the medical treatment concerned, in this case as a histamine $H_1$-antagonist for treatment of, for example, asthma, hayfever, rhinitis or allergic eczema.

Each dosage unit for oral administration contains preferably from 5 to 200 mg of a compound of formula (1) or a pharmaceutically acceptable salt thereof calculated as the free base.

The invention also includes a method of blocking histamine $H_1$-receptors which comprises administering to a subject an effective amount to block said receptors of a compound of formula (1).

The compounds of the invention will normally be administered to a subject for the treatment of rhinitis, hayfever, bronchial asthma or allergic eczema. An adult patient will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLE 1

(i) 2-Bromopyridine (20 g), 1,3-diaminopropane (47 g) and pyridine (13 ml) were heated together under reflux for 2.5 hr. Excess of diaminopropane was evaporated at reduced pressure and the residue was dissolved in water. The pH of the solution was adjusted to pH 14 and extracted with chloroform. The extracts were dried ($K_2CO_3$), and the chloroform was evaporated. The residue was distilled at reduced pressure to give 2-(3-aminopropylamino)pyridine 13.3 g (70%) b.p. 90°–91° C., 0.02 mm Hg.

(ii) Sodium hydride (1.14 g) was dissolved in dimethylsulphoxide (DMSO) (20 ml) at 70°–75° C. The solution was cooled and 2-(3-aminopropylamino)pyridine (6.57 g) in DMSO (20 ml) was added at room temperature. N-Propyl iodide (8.13 g) in DMSO (10 ml) was added dropwise maintaining the temperature at 20°–25° C. After allowing the mixture to stand overnight, water (250 ml) was added and this mixture was extracted with ether. The ether extracts were washed with hydrochloric acid (2N) and the aqueous layers made alkaline to pH 10.5. The aqueous layer was extracted with ether and chloroform. The pH was adjusted to pH 14 and the aqueous layer was extracted again with ether. The final ether extract was dried ($K_2CO_3O$, and the ether was evaporated to give 2-[N-(3-aminopropyl)-N-propylamino]pyridine (3.4 g) as an oil which was used without further purification.

(iii) A solution of 2-[N-(3-aminopropyl)-N-propylamino]pyridine (1.5 g) in methanol (15 ml) was added dropwise over 30 min. to a stirred suspension of 3,4-dimethoxy-1,2,5-thiadiazole-1-oxide (1.26 g) in methanol (45 ml) at 0°–5° C. After having kept the mixture at 5°–10° C. for 2.5 hr., benzylamine (1.25 g) was added dropwise at 5° C. The solution was stirred at room temperature for 2 hr. and then evaporated to dryness. The residue was triturated with wet ether to give, after crystallisation from ethanol, 3-[3-(N-propyl-N-2-pyridylamino)propylamino]-4-benzylamino-1,2,5-thiadiazole-1-oxide (2.07 g, 67%) m.p. 123°–125° C.

$C_{20}H_{26}N_6OS$ Found: C 60.30, H 6.76, N 21.31, S 7.78. Requires: C 60.27, H 6.58, N 21.09, S 8.05

EXAMPLE 2

A solution of 2-[N-(3-aminopropyl)-N-propylamino]-pyridine (1.5 g) in methanol (15 ml) was added dropwise over 30 min. to a stirred suspension of 3,4-dimethoxy-1,2,5-thiadiazole-1-oxide (1.26 g) in methanol (45 ml) at 0°–5° C. After having kept the mixture at 5°–10° C. for 2.25 hr., 2-phenylethylamine (1.41 g) was added dropwise at 5° C. and the solution allowed to warm to room temperature. The mixture was stirred for 2.5 hr. and then evaporated to dryness. The residue was chromatographed (silica gel, dichloromethane/methanol, 40:1) to give an oil which was dissolved in ethanol. Ethanolic hydrogen chloride was added to this solution and the mixture obtained was diluted with an excess of ether to precipitate 3-[3-(N-propyl-N-2-pyridylamino)propylamino]-4-(2-phenylethylamino)-1,2,5-thiadiazole-1-oxide dihydrochloride, 0.5H$_2$O (2.34 g, 61%) m.p. 145°–147° C.

$C_{21}H_{28}N_6OS\cdot2HCl\cdot0.5H_2O$ Found C 51.00, H 6.27, N 17.16, S 6.52, Cl 14.07. Requires: C 50.97, H 6.32, N 16.98, S 6.48, Cl 14.33.

EXAMPLE 3

A solution of 2-{N-(3-aminopropyl)-N-propylamino]-pyridine (1.5 g) in methanol (15 ml) was added dropwise over 30 min. to a stirred suspension of 3,4-dimethoxy-1,2,5-thiadiazole-1-oxide (1.26 g) in methanol (45 ml) at 0°–5° C. After having kept the mixture at 5°–10° C. for 2.25 hr., 3-phenylpropylamine (1.57 g) was added at 5° C. and the solution allowed to warm to room temperature. The mixture was allowed to stand overnight and then evaporated to dryness. The residue was chromatographed (silica gel, eluting with dichloromethane/methanol, 60:1) to give, after crystallisation from ethanol, 3-[3-(N-propyl-N-2-pyridylamino)propylamino]-4-(3-phenylpropylamino)-1,2,5-thiadiazole-1-oxide (1.96 g; 57%) m.p. 118°–121° C.

$C_{22}H_{30}N_6OS$ Found: C 61.92, H 7.05, N 19.69, S 7.71. Requires: C 61.94, H 7.09, N 19.70, S 7.52.

EXAMPLE 4

Substituting 2-aminomethylpyridine (1.26 g) for 3-phenylpropylamine and using corresponding molar proportions of reagents in the method of Example 3 gave, after chromatography (silica gel, dichloromethane/methanol 40:1), and crystallisation from ethanol, 3-[3-(N-propyl-N-2-pyridylamino)propylamino]-4-(2-pyridylmethyl)amino-1,2,5-thiadiazole-1-oxide (1.70 g; 55%) m.p. 127°–129° C.

$C_{19}H_{25}N_7OS$ Found: C 57.02, H 6.46, N 24.65, S 7.97. Requires: C 57.12, H 6.31, N 24.54, S 8.03.

EXAMPLE 5

Substituting 4-aminomethylpyridine (0.84 g) for 3-phenylpropylamine and using corresponding molar proportions of reagents in the method of Example 3 gave, after chromatography (silica gel, chloroform/methanol 6:1) and crystallisation from ethanol, 3-[3-(N-propyl-N-2pyridylamino)propylamino]-4-(4-pyridylmethyl)amino-1,2,5-thiadiazole-1-oxide (0.9 g; 48%) m.p. 136°–137° C.

$C_{19}H_{25}N_7OS$ Found: C 57.39, H 6.34, N 24.36, S 7.90. Requires: C 57.12, H 6.31, N 24.54, S 8.03.

EXAMPLE 6

(i) 2-Bromopyridine (10 g), 1,4-diaminobutane (35 ml) and pyridine (7 ml) were heated together under reflux for 4 hr. The excess of diaminobutane was evaporated at reduced pressure and the residue was dissolved in water. The solution was extracted with chloroform at pH 7 and then made alkaline to pH 13. The alkaline aqueous solution was extracted with more chloroform and was dried (K$_2$CO$_3$). The chloroform was evaporated and the residue was distilled at reduced pressure to give 2-(4-aminobutylamino)pyridine 7.0 g (67%) b.p. 136°–138° C., 2 mm Hg.

(ii) Sodium hydride (1.1 g) was dissolved in DMSO (20 ml) at 70°–75° C. under nitrogen. The solution was cooled and a solution of 2-(4-aminobutylamino)pyridine (6.9 g) in DMSO (20 ml) added at room temperature. N-Propyl iodide (7.81 g) in DMSO (10 ml) was added dropwise maintaining the temperature at 25°–35° C. After a further 15 min. water (200 ml) was added and the mixture was extracted with ether. The ether extract was washed with hydrochloric acid (2N) and the aqueous layer made alkaline to pH 6. After extracting with chloroform, the pH of the aqueous layer was raised to pH 14 and extracted with ether. The ether extracts were washed with 0.1N sodium hydroxide, dried (K$_2$CO$_3$) and the ether evaporated to give 2-[N-(4-aminobutyl)-N-propylamino]pyridine (5.79 g) as an oil which was used without further purification.

(iii) 2-[N-(4-Aminobutyl)-N-propylamino]pyridine (1 g) in methanol (20 ml) was added dropwise to a stirred solution of 3,4,-dimethoxy-1,2,5-thiadiazole-1-oxide (0.78 g) in methanol (70 ml) at 5° C. After having kept the mixture at 5°–10° C. for 3 hr., a solution of 4-aminomethylpyridine (0.78 g) in methanol (20 ml) was added dropwise at 5° C. The mixture was allowed to stand at room temperature overnight and then evaporated to dryness. The residue was chromatographed (silica gel, chloroform/methanol, 20:1) to give, after crystallisation from ethanol, 3-[4-(N-propyl-N-2-pyridylamino)butylamino]-4-(4-pyridylmethylamino)-1,2,5-thiadiazole-1-oxide (1.19 g; 60%) m.p. 128°–130° C.

$C_{20}H_{27}N_7OS$ Found: C 58.19, H 6.72, N 23.87, S 7.96. Requires: C 58.09, H 6.58, N 23.71, S 7.75.

EXAMPLE 7

(i) A solution of 2-(N-phenylamino)pyridine (5.0 g) in DMSO (15 ml) was added to a suspension of sodium hydride (0.78 g) in DMSO (20 ml). The mixture was stirred and slowly heated under nitrogen to 85° C. After the evolution of hydrogen had ceased, the mixture was cooled to room temperature and a solution of N-(3-bromopropyl)phthalimide (7.88 g) in DMSO (15 ml) added dropwise. The mixture was allowed to stand overnight and then poured into water. The aqueous phase was made acid to a pH between 2 to 4 and extracted with ether. The extracts were dried (MgSO$_4$), the ether evaporated and the residue crystallised from ethanol to give N-[3-(N-phenyl-N-pyrid-2-ylamino)-propyl]phthalimide, 3.69 g (35%) m.p. 103°-105° C.

(ii) A mixture of N-[3-(N-phenyl-N-pyrid-2-ylamino)-propyl]phthalimide, (3.1 g) and conc. hydrochloric acid (30 ml) were heated under reflux for 21 hr. Phthalic acid was filtered off on cooling and the solvent was evaporated from the filtrate. The residue was dissolved in water and the solution extracted at pH 1 with chloroform. The pH was raised to pH 13 (NaOH) and the solution extracted again with ether. The ether extracts were dried ($K_2CO_3$) and the ether was evaporated to give 2-[N-(3-aminopropyl)-N-phenylamino]pyridine, 1.84 g as an oil.

(iii) A solution of 2-[N-(3-aminopropyl)-N-phenylamino]pyridine (1.0 g) in methanol (10 ml) was added dropwise to a stirred suspension of 3,4-dimethoxy-1,2,5-thiadiazole-1-oxide (0.71 g) in methanol (30 ml) at 0°-5° C. After having kept the mixture at 5°-10° C. for 2 hr., 4-aminomethylpyridine (0.71 g) was added dropwise at 5° C. The mixture was allowed to stand overnight at room temperature. More 4-aminomethylpyridine (0.5 g) was added, the mixture left overnight and then evaporated to dryness. The residue was chromatographed (silica gel, dichloromethane/methanol 40:1 rising to dichloromethane/methanol 20:1) to give, after crystallisation from ethanol, 3-[3-(N-phenyl-N-2-pyridylamino)propylamino]-4-(4- pyridylmethyl)amino-1,2,5-thiadiazole-1-oxide (0.9 g; 47%) m.p. 139°-141° C.

$C_{22}H_{23}N_7OS$ Found: C 60.98, H 5.33, N 22.54, S 7.33. Requires: C 60.95, H 5.35, N 22.62, S 7.40.

EXAMPLE 8

(i) A mixture of sodium hydride (0.92 g) and 2-(3aminopropylamino)pyridine (5 g) in toluene (100 ml) was heated under nitrogen to 90° C. until initial reaction ceased, and then under reflux for 2 hr. After cooling, 2-bromopyridine (5.53 g) was added and the mixture heated under reflux for 10 hr. The mixture was poured on to ice/water (100 ml), extracted at pH 14 with chloroform, and these extracts washed with 2N HCl. The acidic aqueous solution was adjusted to pH 9 and extracted with ether and the extracts were discarded. The aqueous phase was adjusted to pH 14 and extracted with ether and the latter ethereal extracts were washed with water, dried ($K_2CO_3$) and concentrated to give 3-(N,N-dipyrid-2-ylamino)propylamine (2.93 g, 39%) as an oil which was used without further purification.

(ii) Substituting 3-(N,N-dipyrid-2-ylamino)propylamine (1.0 g) for 2-[N-(4-aminobutyl)-N-propylamino]pyridine and using corresponding molar proportions of other reagents in the method of Example 6(iii) gave, after chromatography (silica gel, dichloromethane:methanol 25:1) 3-[3-(N,N-dipyrid-2-ylamino)propylamino]-4-pyrid-4-ylmethylamino-1,2,5-thiadiazole-1-oxide which was treated with 1.2 equivalents of maleic acid in hot ethanol to give the maleate salt (crystallised from ethanol) (0.52 g, 22%) m.p. 127°-129° C.

$C_{21}H_{22}N_8OS.C_4H_4O_4$ Found C 54.31 H 4.69 N 20.21 S 5.93. Requires C 54.53 H 4.76 N 20.35 S 5.82.

EXAMPLE 9

A pharmaceutical composition for oral administration is prepared containing

|   |   | % by weight |
|---|---|---|
| A | 3-[3-(N—propyl-N—2-pyridylamino)propylamino]-4-(4-pyridylmethyl)amino-1,2,5-thiadiazole-1-oxide | 55 |
|   | Dibasic calcium phosphate dihydrate | 20 |
|   | Approved coloring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellulose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

EXAMPLE 10

A pharmaceutical composition for injectable administration is prepared by forming a solution of 3-[3-(N-propyl-N-2-pyridylamino)propylamino]-4-(4-pyridylmethyl) amino-1,2,5-thiadiazole-1-oxide in sterile water to give a 1 to 5% w/w solution. The solution is clarified by filtration and filled into vials which are sealed and sterilised. A suitable vial contains 2 ml of the solution.

What is claimed is:

1. A compound of formula (1):

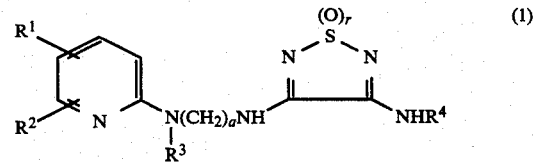

or a pharmaceutically acceptable salt thereof, where:
$R^1$ and $R^2$ are the same or different and are hydrogen, $C_{1-6}$alkyl, $C_{1-6}$alkoxy or halogen;
$R^3$ is $C_{1-6}$alkyl or optionally substituted phenyl or optionally substituted pyridyl, where the optional substituents are one or more $C_{1-6}$alkyl, $C_{1-6}$alkoxy, or hydroxy groups or halogen atoms;
a is from 2 to 4
$R^4$ is $(CH_2)_bR^5$ where b is 1–6 and
$R^5$ is
phenyl optionally substituted by one or more $C_{1-6}$alkyl, $C_{1-6}$alkoxy, hydroxy, carboxy (or an $C_{1-6}$ alkyl ester thereof) or sulphonamido groups or halogen atoms;
pyridyl optionally substituted by one or more $C_{1-6}$alkyl, $C_{1-6}$alkoxy or hydroxy groups or halogen atoms;
or N-oxo-pyridyl optionally substituted by $C_{1-6}$alkyl; and
r is 1 or 2.

2. A compound as claimed in claim 1 where $R^1$ and $R^2$ are both hydrogen.

3. A compound as claimed in claim 1 or claim 2 where a is 3.

4. A compound as claimed in claim 1 where $R^3$ is phenyl or $C_{1-6}$alkyl.

5. A compound as claimed in claim 4 where $R^3$ is n-propyl.

6. A compound as claimed in claim 1 where b is 1.

7. A compound as claimed in claim 6 where $R^5$ is phenyl or 4-pyridyl.

8. A compound as claimed in claim 1 where r is 1.

9. A compound of claim 1, said compound being 3-[3-(N-propyl-N-2-pyridylamino)propylamino]-4-benzylamino-1,2,5-thiadiazole-1-oxide or a pharmaceutically acceptable acid addition salt thereof.

10. A compound of claim 1, said compound being 3-[3-(N-propyl-N-2-pyridylamino)propylamino]-4-(2-phenylethylamino)-1,2,5-thiadiazole-1-oxide or a pharmaceutically acceptable acid addition salt thereof.

11. A compound of claim 1, said compound being 3-[3-(N-propyl-N-2-pyridylamino)propylamino]-4-(3-phenylpropylamino)-1,2,5-thiadiazole-1-oxide or a pharmaceutically acceptable acid addition salt thereof.

12. A compound of claim 1, said compound being 3-[3-(N-propyl-N-2-pyridylamino)propylamino]-4-(2-pyridylmethylamino)-1,2,5-thiadiazole-1-oxide or a pharmaceutically acceptable acid addition salt thereof.

13. A compound of claim 1, said compound being 3-[3-(N-propyl-N-2-pyridylamino)propylamino]-4-(4-pyridylmethylamino)-1,2,5-thiadiazole-1-oxide or a pharmaceutically acceptable acid addition salt thereof.

14. A compound of claim 1, said compound being 3-[4-(N-propyl-N-2-pyridylamino)butylamino]-4-(4-pyridylmethylamino)-1,2,5-thiadiazole-1-oxide or a pharmaceutically acceptable acid addition salt said thereof.

15. A compound of claim 1, said compound being 3-[3-(N-phenyl-N-2-pyridylamino)propylamino]-4-(4-pyridylmethylamino)-1,2,5-thiadiazole-1-oxide or a pharmaceutically acceptable acid addition salt thereof.

16. A compound of claim 1, said compound being 3-[3-(N,N-dipyrid-2-ylamino)propylamino]-4-(pyrid-4-ylmethylamino)-1,2,5-thiazole-1-oxide or a pharmaceutically acceptable acid addition salt thereof.

17. A pharmaceutical compound for blocking histamine $H_1$-receptors which comprises an effective amount to block said receptors of a compound according to claim 1 and a carrier.

18. A method of blocking histamine $H_1$-receptors which comprises administering to a subject an effective amount to block said receptors of a compound according to claim 1.

* * * * *